United States Patent

Leising et al.

Patent Number: 5,665,024
Date of Patent: Sep. 9, 1997

[54] METHOD OF DETECTING DETERIORATION OF AUTOMATIC TRANSMISSION FLUID

[75] Inventors: Maurice B. Leising, Clawson; Hans Dourra, Dearborn; Howard L. Benford, Bloomfield Hills, all of Mich.

[73] Assignee: Chrysler Corporation, Auburn Hills, Mich.

[21] Appl. No.: 623,267

[22] Filed: Mar. 28, 1996

[51] Int. Cl.⁶ .................................................. B60K 41/02
[52] U.S. Cl. ............................ 477/61; 477/65; 477/176
[58] Field of Search ........................... 477/61, 65, 120, 477/169, 176

[56] References Cited

U.S. PATENT DOCUMENTS

| | | | |
|---|---|---|---|
| 4,206,613 | 6/1980 | Shockley | 62/133 |
| 4,289,100 | 9/1981 | Kinugawa et al. | 123/339 |
| 4,312,311 | 1/1982 | Iwata | 123/339 |
| 4,325,330 | 4/1982 | Kugler et al. | 123/41.12 |
| 4,391,242 | 7/1983 | Mashio | 123/198 R |
| 4,480,443 | 11/1984 | Nishi et al. | 62/227 |
| 4,481,784 | 11/1984 | Elmslie | 62/133 |
| 4,494,641 | 1/1985 | Sakakiyama | 192/0.08 |
| 4,530,338 | 7/1985 | Sumi | 123/559 |
| 4,556,942 | 12/1985 | Russo et al. | 364/431.07 |
| 4,658,943 | 4/1987 | Nishikawa et al. | 192/0.073 |
| 4,688,530 | 8/1987 | Nishikawa et al. | 123/198 R |
| 4,723,416 | 2/1988 | Suzuki | 62/226 |
| 4,796,438 | 1/1989 | Sato | 62/133 |
| 4,898,005 | 2/1990 | Sakurai | 62/115 |
| 4,926,651 | 5/1990 | Noguchi | 62/133 |
| 4,976,589 | 12/1990 | Ide | 417/34 |
| 5,018,362 | 5/1991 | Nagase et al. | 62/133 |
| 5,056,326 | 10/1991 | Ohkumo et al. | 62/133 |
| 5,111,718 | 5/1992 | Iizuka | 74/866 |
| 5,117,643 | 6/1992 | Sakurai et al. | 62/133 |
| 5,167,127 | 12/1992 | Ohtsu | 62/133 |
| 5,203,178 | 4/1993 | Shyu | 62/180 |
| 5,257,507 | 11/1993 | Taguchi | 62/133 |
| 5,285,649 | 2/1994 | Yamanaka et al. | 62/133 |
| 5,341,295 | 8/1994 | Nakagawa et al. | 364/424.1 |
| 5,347,824 | 9/1994 | Kato et al. | 62/133 |
| 5,349,826 | 9/1994 | Kawai et al. | 62/133 |
| 5,415,004 | 5/1995 | Iizuka | 62/133 |

*Primary Examiner*—Dirk Wright
*Attorney, Agent, or Firm*—Roland A. Fuller

[57] ABSTRACT

A method of determining the deterioration of automatic transmission fluid by detecting shudder during the EMCC portion of air conditioner clutch engagement. Shudder is detected by calculating the acceleration of the turbine during EMCC slip with the following equation:

$$\Sigma\alpha_t = \Sigma\alpha_t(i-1) + \alpha_t$$

where $\alpha_t$ represents the absolute value of turbine acceleration. In a preferred embodiment, the turbine acceleration is summed for twenty-eight periods of 7 msec each after the start of EMCC and the determination that shudder occurred made if the resulting value exceeds a predetermined number. In a further preferred embodiment, the method is used to modify the air conditioner compressor clutch engagement sequence. Once it is determined that shudder is occurring during the EMCC portion of the air conditioner compressor clutch engagement sequence, the EMCC portion of the air conditioner clutch engagement sequence is eliminated or bypassed.

15 Claims, 2 Drawing Sheets

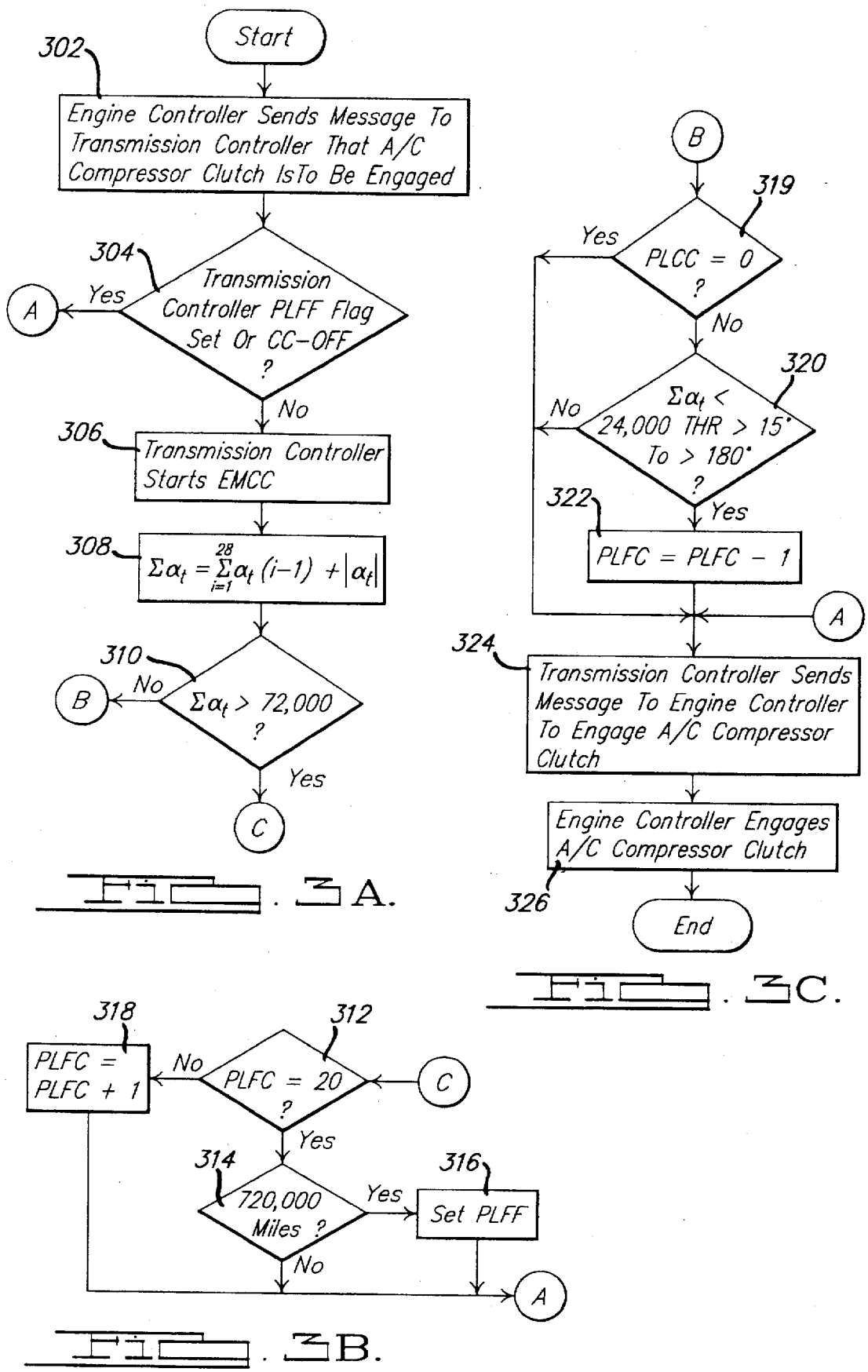

METHOD OF DETECTING DETERIORATION OF AUTOMATIC TRANSMISSION FLUID

This invention relates to a method of engaging the compressor clutch of an automotive air conditioner compressor, and more particularly, to a method of detecting when automatic transmission fluid has deteriorated and altering the method in which the compressor clutch is engaged based on whether the automatic transmission fluid has deteriorated.

BACKGROUND

In motor vehicles having automatic transmissions and air conditioning systems, engagement of the air conditioner compressor clutch when the transmission converter clutch is engaged or on (CC-ON) has resulted in an objectionable disturbance. One solution to this problem involves a specific sequence of steps in the engine and transmission control to engage the compressor clutch. First, the engine controller sends a message to the transmission controller that the air conditioner compressor clutch is to be engaged. The transmission controller then starts electronic modulation (EMCC) of the transmission converter clutch. When slip occurs, i.e., engine and turbine speed are separated, the transmission controller sends a message to the engine controller. The engine controller then engages the air conditioner compressor clutch.

The problem with the above is that if the automatic transmission fluid has deteriorated sufficiently, there is a risk that acceptable EMCC cannot be established due to an induced system shudder. When automatic transmission fluid deteriorates (friction coefficient characteristics change), the transmission system is no longer capable of keeping EMCC operation under control when slip starts and a large disturbance or shudder typically occurs when slip starts.

It is an object of this invention to avoid the foregoing problem by determining that the automatic transmission fluid has deteriorated and when it has, bypassing the EMCC portion of the air conditioner compressor clutch engagement sequence.

It is another object of this invention to determine that the automatic transmission fluid has deteriorated by detecting shudder during the EMCC portion of the air conditioner compressor clutch engagement sequence.

SUMMARY OF THE INVENTION

According to the method of this invention, deterioration of automatic transmission fluid is determined by detecting shudder during the EMCC portion of air conditioner clutch engagement. Shudder is detected by calculating the acceleration of the turbine during initial periods of EMCC with the following equation:

$$\Sigma \alpha_t = \Sigma \alpha_t(i-1) + \alpha_t$$

where $\alpha_t$ represents the absolute value of turbine acceleration. In a preferred embodiment, the absolute value of turbine acceleration is summed for twenty-eight periods of 7 msec each and the determination that shudder occurred made if the resulting value exceeds a predetermined value.

The method of this invention for determining that the automatic transmission fluid has deteriorated by detecting shudder is used to modify the air conditioner compressor clutch engagement sequence. Once it is determined that shudder is occurring during the EMCC portion of the air conditioner compressor clutch engagement sequence, the EMCC portion of the air conditioner clutch engagement sequence is then eliminated or bypassed.

BRIEF DESCRIPTION OF THE DRAWINGS

Additional features and advantages of the invention will become apparent to those skilled in the art upon consideration of the following detailed description of a preferred embodiment exemplifying the best mode of carrying out the invention as presently perceived. The detailed description particularly refers to the accompanying figures in which:

FIGS. 3A–3C are a flow chart of a method of controlling the air conditioner compressor clutch according to this invention.

DETAILED DESCRIPTION

Figure 1:
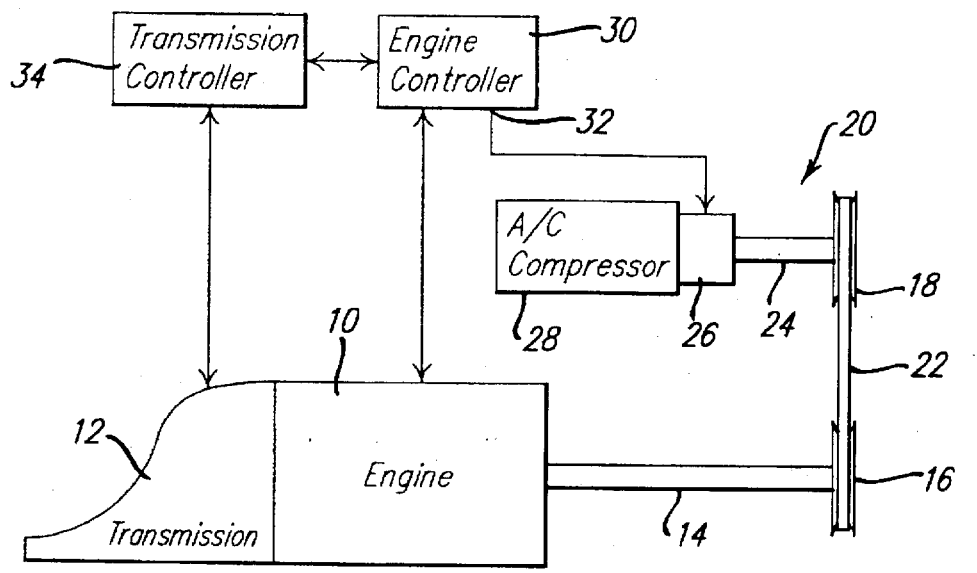
FIG. 1 is a block diagram of an engine and air conditioning system of a motor vehicle.

Referring to FIG. 1, a motor vehicle engine 10 is coupled to a transmission 12 in conventional fashion. Engine 10 also has a crankshaft 14 to which a pulley 16 is affixed. Pulley 16 is coupled to a pulley 18 of air conditioner compressor assembly 20 by a belt 22 in conventional fashion. Pulley 18 of air conditioner compressor assembly 20 is affixed to an input 24 of compressor clutch 26 of air conditioner compressor 28. An engine controller 30 is coupled to engine 10 and has an output 32 coupled to compressor clutch 26 of air conditioner compressor 28. A transmission controller 34 is coupled to transmission 12.

Engine controller 30 and transmission controller 34 are conventional engine and transmission controllers, comprising a microprocessor system having a microprocessor, memory, and related elements. Engine controller 30 and transmission controller 34 can be separate systems or their functions combined in one microprocessor system.

As discussed above, engagement of air conditioner compressor clutch 26 when the converter clutch of the transmission 12 is on causes an objectionable disturbance. One way of eliminating this objectionable disturbance is by an appropriate engagement sequence of air conditioner clutch 26 involving an interaction between engine controller 30 and transmission controller 34.

Figure 2:
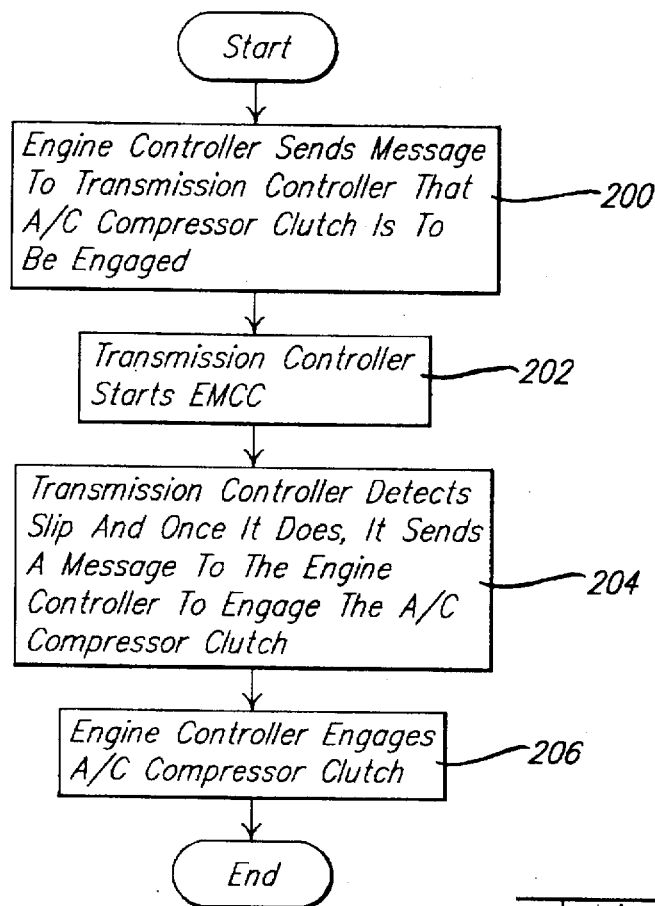
FIG. 2 is a flow chart of a method of controlling the air conditioner compressor clutch.

Referring to FIG. 2, a sequence of steps for engaging the air conditioner clutch to avoid the above problem is shown. When air conditioner clutch 26 is to be engaged, a message is first sent at block 200 from engine controller 30 to transmission controller 34 to this effect. Transmission controller 34 then starts EMCC at block 202. Once slip occurs, transmission controller 34 at block 204 sends a message to engine controller 30 to this effect. Engine controller 30 then engages air conditioner clutch 26 at block 206.

As mentioned, when the automatic transmission fluid deteriorates, transmission controller 34 can no longer keep EMCC under control. Consequently, where the automatic transmission fluid has deteriorated and the above air conditioner clutch 26 engagement sequence used, a large disturbance or shudder occurs.

Referring to FIGS. 3A–3C, a method according to this invention of avoiding such shudder is shown. When air conditioner clutch 26 is to be engaged, a message is first sent at block 302 from engine controller 30 to transmission controller 34 to this effect. Transmission controller 34 then checks to see if the CC is off (CC-OFF) or the partial lock-up failure flag (PLFF) is set at block 304. If so, the routine bypasses EMCC and branches to where the transmission controller sends a message to the engine controller to engage the air conditioner compressor clutch at step 324. If the PLFF flag is not set and the CC is on (CC-ON), the transmission controller 34 starts EMCC at step 306 and goes on to determine if the automatic transmission fluid has deteriorated by detecting shudder during EMCC.

Transmission controller 34 begins to detect shudder during EMCC by determining the absolute value of the acceleration of the turbine in transmission 12 during the first 196 msec of EMCC slip at step 308. Transmission controller 34, as is conventional, monitors the speed and acceleration of the turbine in transmission 12 and is illustratively is on a 7 msec cycle so it sums the absolute value of turbine acceleration over the next twenty-eight cycles after the start of EMCC slip.

Once transmission controller 34 sums the absolute value of turbine acceleration, it determines if shudder is occurring by comparing it to a predetermined value, illustratively 72,000, at step 310. If the value of absolute turbine acceleration sum exceeds 72,000, this means that the average of the value of absolute turbine acceleration sum over the first twenty-eight cycles of EMCC slip has exceeded 2,600 rpm/sec., which indicates that shudder is occurring. Upon this determination, transmission controller 34 next checks at step 312 to see if partial lock-up failure counter (PLFC) has reached twenty. In the preferred embodiment, twenty occurrences of shudder are used as the basis of determining that the automatic transmission fluid has deteriorated so that the EMCC portion of the air conditioner clutch engagement sequence should be bypassed. If the PLFC has not reached twenty, it is incremented by one at step 318 and the routine branches to where the transmission controller sends a message to the engine controller to engage the air conditioner clutch 26 at step 324.

If the PLFC has reached twenty, the transmission controller 34 next checks at step 314 to determine whether the vehicle has at least 20,000 miles. If it does, transmission controller 34 sets PLFF at step 316 and continues to step 324 where transmission controller 34 sends the message to engine controller 30 to engage the air conditioner compressor clutch. If the vehicle has less than 20,000 miles, the PLFF is not set and the routine branches to step 324. Where a vehicle has less than 20,000 miles, it is unlikely that the automatic transmission fluid would have deteriorated so any shudder is likely due to reasons other than deteriorated automatic transmission fluid.

Returning to step 310, if the value of the absolute turbine acceleration sum is less than 72,000, transmission controller 34 next checks at step 319 to see if the PLFC is zero. If so, the routine branches to step 324 where transmission controller 34 sends a message to engine controller 30 to engage the air conditioner compressor clutch 26. If the PLFC was not equal to zero, Transmission controller 34 determines at step 320 if the value of the absolute turbine acceleration sum is less than 24,000, the throttle angle is greater than 15° and the operating temperature of transmission 12 is greater than 180° F. If these conditions are met, transmission controller 34 decrements PLFC at step 322 and continues to step 324. If these conditions are not met, transmission controller 34 branches around step 322 to step 324. This accommodates determining that deteriorated automatic transmission fluid has been changed. In this regard, the PLFF is reset upon each vehicle start so that the routine is tried at least once during each vehicle operation which accommodates changed conditions that might affect the occurrence of shudder, such as changing deteriorated automatic transmission fluid.

Once a message is sent at step 324 by transmission controller 34 to engine controller 30 to engage the air conditioner compressor clutch, engine controller 30 engages the air conditioner compressor clutch at 326.

Although the invention has been described in detail with reference to certain preferred embodiments and specific examples, variations and modifications exist within the scope and spirit of the invention as defined in the following claims.

What is claimed is:

1. In a motor vehicle having an automatic transmission and air conditioner, the automatic transmission having a converter clutch and a turbine, the air conditioner having a compressor, the compressor having a clutch, the compressor clutch being engaged by an engine controller to which it is coupled, the transmission coupled to a transmission controller, the compressor clutch engaged by a sequence of engine controller and transmission controller steps wherein the engine controller sends a message to the transmission controller that the compressor clutch is to be engaged, the transmission controller starts electronic modulation of its converter clutch (EMCC) and, upon detecting slip, sends a message to the engine controller to engage the compressor clutch, the engine controller engaging the compressor clutch upon receipt of the message to do so from the transmission controller, a method of determining that the automatic transmission fluid has deteriorated by detecting whether shudder occurs during an initial period of EMCC slip.

2. The method of claim 1 wherein the step of detecting whether shudder occurred during the initial period of EMCC slip comprises determining acceleration of the transmission's turbine during the initial period, comparing this initial acceleration of the transmission's turbine to a predetermined value, and determining that shudder occurred when the initial acceleration of the transmissions' turbine exceeds the predetermined value.

3. The method of claim 2 wherein the step of determining that shudder occurred when the acceleration of the transmission's turbine exceeds the predetermined value further includes determining that shudder occurred only after the initial acceleration of the transmission's turbine exceeds the predetermined value during EMCC in a plurality of compressor clutch engagement sequences.

4. The method of claim 3 wherein the plurality of compressor clutch engagement sequences are twenty.

5. The method of claim 2 wherein the initial period is about 200 msec.

6. The method of claim 2 wherein the initial period comprises about twenty-eight cycles of the transmission controller after the start of EMCC slip, and the step of determining the initial turbine acceleration comprises summing the absolute values of the turbine acceleration of each cycle.

7. In a motor vehicle having a transmission, the transmission having a turbine, a transmission controller, an air conditioner compressor, the air conditioner compressor having a clutch, a method of engaging the air conditioner clutch to reduce the occurrence of disturbances upon engagement of the clutch, comprising the steps of:

a. sending a message from the engine controller to the transmission controller that the compressor clutch is to be engaged;

b. determining whether the transmission's automatic transmission fluid has deteriorated;

c. electronically modulating the transmissions' converter clutch (EMCC) if the automatic transmission fluid has not deteriorated and determining when slip occurs;

d. bypassing step c if the automatic transmission fluid has deteriorated;

e. sending a message from the transmission controller to the engine controller to engage the compressor clutch; and f. engaging the compressor clutch upon the engine controller's receipt of the message from the transmission controller to engage the compressor clutch.

8. The method of claim 7 wherein the step of determining whether the automatic transmission fluid has deteriorated comprises determining whether shudder has occurred during an initial period of EMCC slip.

9. The method of claim 8 wherein the step of determining whether shudder has occurred during EMCC of a plurality of compressor clutch engagement sequences comprises determining the value of absolute acceleration of the transmission's turbine during each initial period, comparing the initial turbine acceleration value to a first predetermined value and incrementing a counter when the initial turbine acceleration value exceeds the first predetermined value, and the step of determining that the automatic transmission fluid has deteriorated includes doing so when the counter reaches a second predetermined value.

10. The method of claim 9 wherein the step of determining the absolute value of the transmission turbine's absolute initial acceleration comprises summing the absolute values of the transmission turbine's acceleration during the first twenty-eight cycles of the transmission controller after start of EMCC slip.

11. The method of claim 9 wherein the step of determining the absolute average value of the transmission turbine's absolute initial acceleration comprises averaging the absolute values of the transmission's acceleration during the first twenty-eight cycles of the transmission controller after start of EMCC slip.

12. The method of claim 10 wherein the first predetermined value is about 72,000 rpm/sec. and the second predetermined value is about 20.

13. The method of claim 11 wherein the first predetermined value is about 2600 rpm/sec and the second predetermined value is about 20.

14. The method of claim 9 wherein the step of determining that the automatic transmission fluid has deteriorated includes the steps of setting a flag in the transmission controller when the counter reaches the second predetermined value, decrementing the counter if the absolute value of the transmission's turbine's absolute initial acceleration is less than a third predetermined value, the step of determining whether the transmission's automatic transmission fluid has deteriorated so as to bypass step c of claim 7 includes checking the flag and bypassing step c of claim 7 if the flag is set, and further including the step of resetting the flag each time the vehicle is started.

15. The method of claim 9 wherein the third predetermined value is about 24,000 rpm/sec.

* * * * *